(12) United States Patent
Hand et al.

(10) Patent No.: US 9,851,164 B2
(45) Date of Patent: Dec. 26, 2017

(54) LASER CENTERING OF ROBOTIC ARM

(71) Applicant: CoreStar International Corporation, Irwin, PA (US)

(72) Inventors: David A. Hand, North Huntingdon, PA (US); Christopher M. Belville, Jeannette, PA (US); Michael D. Coradi, Pittsburgh, PA (US)

(73) Assignee: CoreStar International Corporation, Irwin, PA (US)

( * ) Notice: Subject to any disclaimer, the term of this patent is extended or adjusted under 35 U.S.C. 154(b) by 377 days.

(21) Appl. No.: 14/645,783

(22) Filed: Mar. 12, 2015

(65) Prior Publication Data

US 2015/0258694 A1  Sep. 17, 2015

Related U.S. Application Data

(60) Provisional application No. 61/952,354, filed on Mar. 13, 2014.

(51) Int. Cl.
| | |
|---|---|
| *G01B 11/00* | (2006.01) |
| *F28F 99/00* | (2006.01) |
| *B25J 9/10* | (2006.01) |
| *B25J 19/02* | (2006.01) |
| *F01K 5/02* | (2006.01) |
| *F28G 1/16* | (2006.01) |
| *F28G 15/08* | (2006.01) |
| *G01N 27/90* | (2006.01) |

(52) U.S. Cl.
CPC ............ *F28F 99/00* (2013.01); *B25J 9/1015* (2013.01); *B25J 19/022* (2013.01); *F01K 5/02* (2013.01); *F28G 1/163* (2013.01); *F28G 15/08* (2013.01); *G01N 27/902* (2013.01); *Y10T 29/49352* (2015.01); *Y10T 29/53113* (2015.01)

(58) Field of Classification Search
CPC ......... G01B 11/27; G01B 11/272; G03F 9/70; G03F 7/70358; H01L 21/681
USPC ........................................................ 356/399
See application file for complete search history.

(56) References Cited

U.S. PATENT DOCUMENTS

| | | | | |
|---|---|---|---|---|
| 4,694,136 A | * | 9/1987 | Kasner .................. | B23K 26/04 219/121.63 |
| 5,483,033 A | * | 1/1996 | Pirl ...................... | B23K 9/0288 219/121.64 |
| 5,491,317 A | * | 2/1996 | Pirl ...................... | B23K 26/106 219/121.63 |
| 5,904,864 A | * | 5/1999 | Nester .................. | B23K 9/0288 219/124.34 |

\* cited by examiner

*Primary Examiner* — Tarifur Chowdhury
*Assistant Examiner* — Md M Rahman
(74) *Attorney, Agent, or Firm* — The Webb Law Firm

(57) ABSTRACT

In a system and method of working tubes coupled to a tubesheet having a number of holes, wherein each hole in fluid communication with one of the tubes, an end-effector is positioned by a robot in coarse or rough alignment with a first hole in the tubesheet. Via lasers positioned on the end-effector, laser spots are formed on a surface of the tubesheet adjacent the first hole. The laser spots are detected by a camera and the alignment of the end-effector relative to the first hole in the tubesheet is refined via the robot based on the detected pattern of laser spots. The tool is then moved into the tube that is in fluid communication with the first hole in the tubesheet to work on (inspect, plug, sleeve or weld) the tube.

16 Claims, 6 Drawing Sheets

LASER CENTERING OF ROBOTIC ARM

CROSS REFERENCE TO RELATED APPLICATION

This application claims the benefit of U.S. Provisional Application No. 61/952,354, filed Mar. 13, 2014, which is incorporated herein by reference.

BACKGROUND OF THE INVENTION

Field of the Invention

The present invention relates to working of tubes coupled to a tubesheet and, more particularly, to the use of robotics and light sources for such working.

Description of Related Art

In nuclear steam generator and balance of plant eddy current inspections, robots are often used to position a tool in alignment with one or more given tubes, one-at-a-time, in a tubesheet. The robot has an end-effector that supports the tool in position to be fed into holes in the tubesheet. The tool must be positioned directly in alignment with the tube to be inspected in order for the tool to run smoothly through the hole in a tubesheet and into the tube in fluid communication with the hole in the tubesheet.

Typically, a camera mounted on the end-effector is utilized to monitor the alignment of the tool to a particular hole in the tubesheet. Because the viewing axis of the camera is mounted transverse to the axis of the tubesheet and, hence, the hole desired to be aligned with the tool, an image of the end of the tool and the hole being aligned therewith suffers from a condition known as parallax which is the apparent displacement of an observed object due to a change in the position of the observer.

Because of this parallax, it is not uncommon to misalign the tool and a hole in a tubesheet, whereupon the tool cannot be successfully inserted into the desired hole in the tubesheet because of this misalignment. Because the insertion of the tool into each tube is often controlled by a motorized drive, there is a chance when the tool is misaligned with a hole in the tubesheet that the motorized drive will push the tool into the face of the tubesheet, instead of the hole thereby potentially damaging the tool.

SUMMARY OF THE INVENTION

Disclosed herein is method of working tubes coupled to a tubesheet having a plurality of holes, each hole in fluid communication with one of the tubes. The method includes: (a) providing a robot positioned in operable relation to the tubesheet, a guide-tube supported by the robot, a tool supported by the guide-tube and movable relative to the guide-tube, a camera coupled to the robot, and a plurality of lasers positioned around an exterior of the guide-tube and operable to output a plurality of laser beams toward the tubesheet; (b) via the robot, positioning the guide-tube in coarse alignment with a first hole in the tubesheet; (c) via the camera, detecting a pattern of laser spots formed by the laser beams on a surface of the tubesheet adjacent the first hole in the tubesheet; (d) via the robot, refining the alignment of the guide-tube in alignment with the first hole in the tubesheet based on the detected pattern of laser spots formed on the surface of the tubesheet; and (e) moving the tool into the tube that is in fluid communication with the first hole in the tubesheet.

The method can further include: (f) withdrawing the tool from the tube that is in fluid communication with the first hole in the tubesheet.

The method can further include repeating steps (b)-(f) for at least one other hole of the tubesheet.

The positioning in step (b) can be with or without reference to the laser spots formed by the laser beams on the surface of the tubesheet.

Following step (d), the guide-tube, the tool, the first hole, and the tube that is in fluid communication with the first hole can be positioned coaxially or substantially coaxially.

The robot can have two axes of rotation and/or a linear axis of motion.

The camera has a viewing axis that is non-parallel with an axis of the first hole.

The pattern of laser spots can be an arc or a ring of laser spots adjacent the first hole. Step (d) can include refining the alignment of the guide-tube in alignment with the first hole in the tubesheet based on a symmetry of the arc or a ring of laser spots around the first hole.

Also disclosed is a method of working tubes coupled to a tubesheet having a plurality of holes, each hole in fluid communication with one of the tubes. The method includes: (a) positioning a tool in alignment with a first hole in the tubesheet; (b) projecting a light pattern onto a surface of the tubesheet adjacent an outer boundary of the first hole; and (c) moving the tool into the tube that is in fluid communication with the first hole in the tubesheet based on the projected light path.

The method can further include, between steps (b) and (c), the step of: (b2) refining the alignment of the tool in alignment with the first hole in the tubesheet based on a symmetry of the light pattern projected onto the surface of the tubesheet about the first hole.

The method can further include: (d) withdrawing the tool from the tube that is in fluid communication with the first hole in the tubesheet based on the projected light pattern.

Refining the alignment of the tool with the first hole in the tubesheet can further include turning the light pattern on and off.

The method can further include repeating any combination of steps (a), (b), (b2), (c) or (d) for a plurality of other holes of the tubesheet.

The light pattern can define an arc or a ring of light. The method can further include refining the alignment of the tool in alignment with a first hole in the tubesheet based on the light pattern projected onto the surface of the tubesheet. Refining the alignment can include refining the symmetry of the arc or ring of light about the first hole.

The light pattern can be one of the following: a plurality of spots of light, a cross hair, or a circle.

The plurality of spots of light can include light spots of different colors.

The method can further include determining whether the tool is out of the tube or in the tube based on being able to observe the entire light pattern or not, respectively.

Lastly, disclosed herein is a system for working tubes coupled to a tubesheet having a plurality of holes, each hole in fluid communication with one of the tubes. The system comprises: a multi-axis robot positioned in operable relation to the tubesheet; an end-effector supported by the robot; a tool supported by the end-effector and movable relative to the end-effector; a camera supported by the robot with an axis of the camera transverse to an axis of a hole in the tubesheet; and one or more lasers supported by the end-effector and operable to output laser beams in a direction of the tubesheet.

The one or more laser beams can be output parallel with the axis of the hole.

The tool can be positioned inside a guide-tube.

The system can include the one or more lasers are positioned about an exterior of the guide-tube.

The system can include a controller operative for controlling: movement of the robot to position the tool in alignment with each of a plurality of holes, one-at-a-time, based on camera images of a pattern of laser light formed by the projection of the one or more laser beams on the tubesheet adjacent the hole; and movement of the tool into and out of the tube in fluid communication with the hole.

The controller can be operative under the control of a control software program to enable the movement of the robot, the movement of the tool, or both to be controlled under manual, user control, automatic control, or a combination of manual control and automatic control.

The tool can be an eddy current probe.

The controller can be operative for turning the one or more lasers on and off and for positioning the tool based on first and second camera images acquired with the one or more lasers on and off, respectively.

The method of claim 10, wherein refining the alignment of the tool with the first hole in the tubesheet further includes turning the light pattern on and off.

DETAILED DESCRIPTION OF THE INVENTION

The present invention will be described with reference to the accompanying figures where like reference numbers correspond to like elements.

Figure 1A:
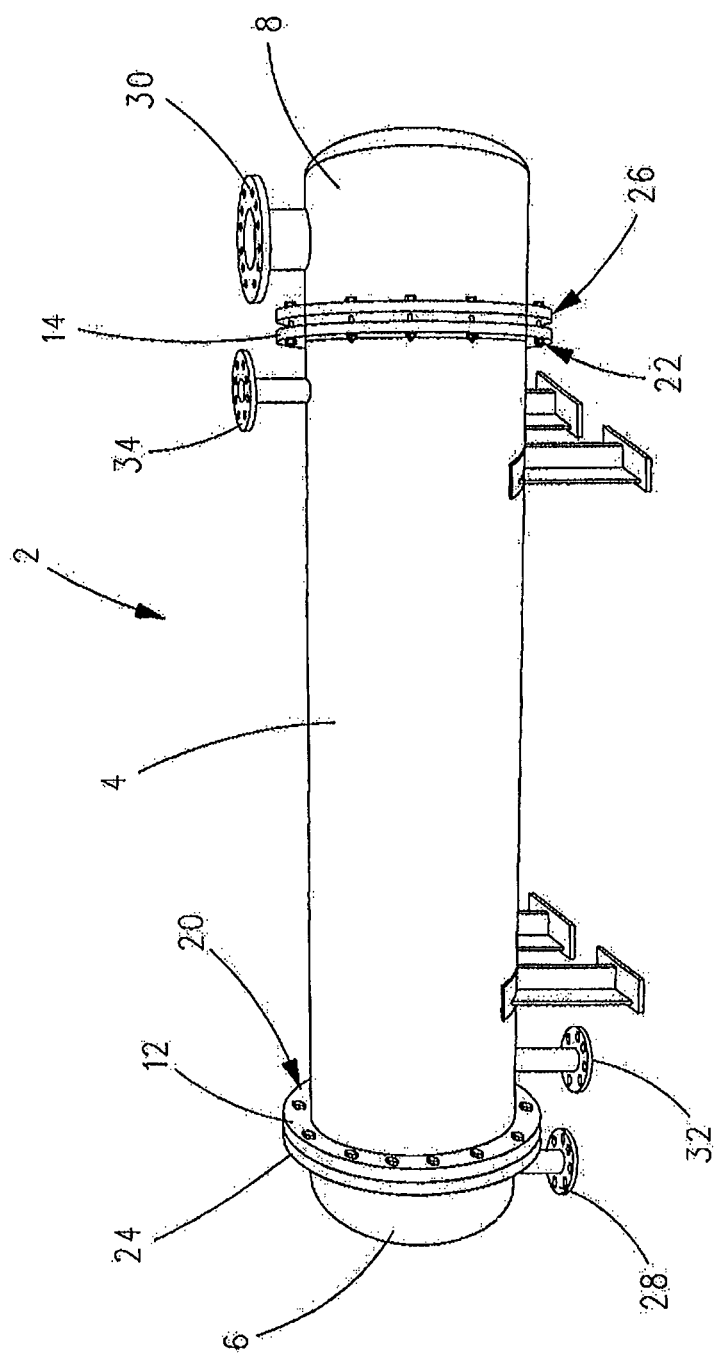
FIG. 1A is a perspective view of the side of a prior art industrial fluid-to-fluid heat exchanger.
Figure 1B:
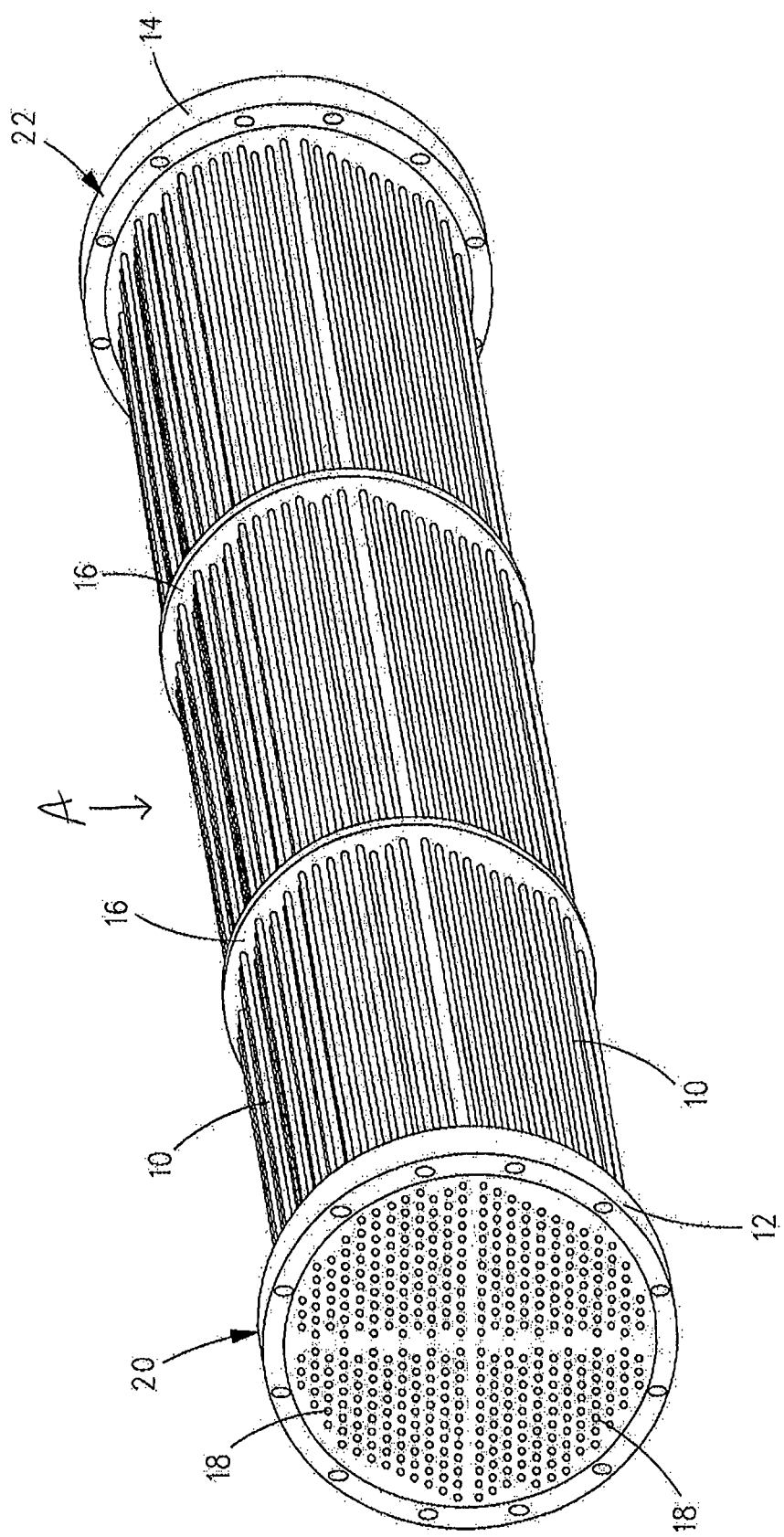
FIG. 1B is a perspective view of an internal assembly of the heat exchanger shown in FIG. 1A including a pair of tubesheets at opposite ends and heat exchange tubes extending between the tubesheets.
Figure 1C:
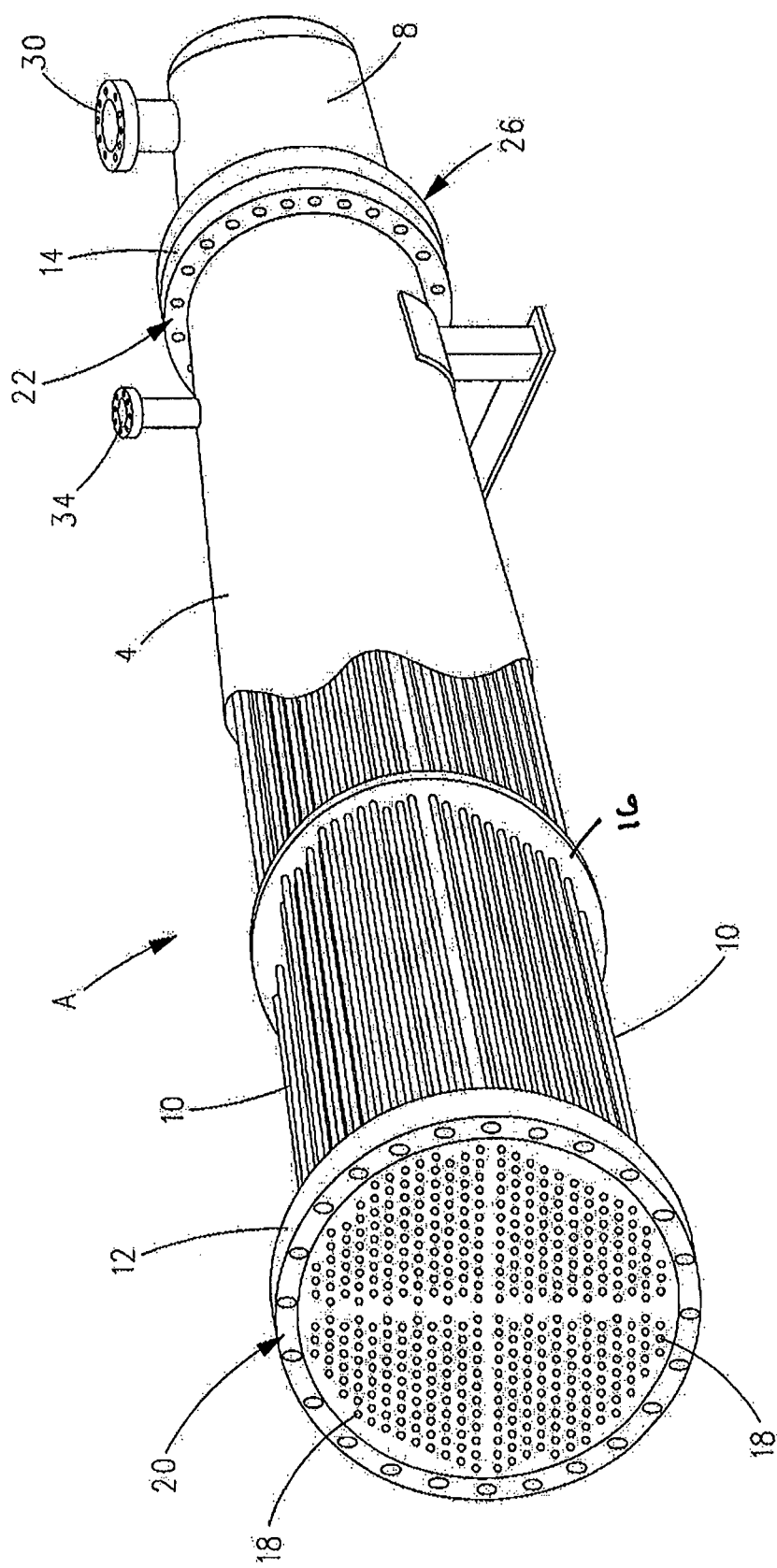
FIG. 1C is a cutaway perspective view of the heat exchanger of FIG. 1A including the internal assembly of FIG. 1B disposed in the heat exchanger housing.

With reference to FIGS. 1A-C, an industrial liquid-to-liquid heat exchanger 2 found in many industrial applications, such as, without limitation, a nuclear steam generation power plant, includes an elongated cylindrical housing 4 with end caps 6 and 8 coupled to opposite ends of housing 4. Disposed within housing 4 is an internal assembly A that includes a plurality of heat exchange tubes 10 that are held in spaced relation by tubesheets 12 and 14 at opposite ends of tubes 10 and optionally one or more support plates 16 positioned between tubesheets 12 and 14.

Each tubesheet 12 and 14 includes a plurality of holes 18 that extend therethrough. Each hole 18 is in fluid communication with one of the tubes 10. Tubesheets 12 and 14 include flanges 20 and 22 that are configured to mate with flanges 24 and 26 of end caps 6 and 8, respectively, in the assembled heat exchanger 2. Suitable fasteners (not numbered) are utilized to secure flanges 20 and 24 together and to secure flanges 22 and 26 together.

In the assembled heat exchanger shown in FIG. 1A, the interiors of end caps 6 and 8 are in fluid communication via tubes 10 of internal assembly A disposed within the interior of housing 4. Suitable fluid-tight seals can be disposed between assembled flanges 20 and 24 and assembled flanges 20 and 22 to maintain the fluid-tight integrity of end caps 4 and 10 to housing 4, and avoid fluid inside of end cap 6 or end cap 8 from seeping into the interior of housing 4, or vice versa.

End caps 6 and 8 include ports 28 and 30, respectively. In use, fluid entering one of port 28 and 30 passes exclusively through holes 18 in tubesheets 12 and 14 and tubes 10 disposed in housing 4 and exits the other of port 28 and 30.

Housing 4 includes ports 32 and 34 at opposite ends thereof. In use, fluid introduced into one of ports 32 and 34 passes through the interior of housing 4 contacting the exterior of tubes 10 disposed in housing 4 and exits the other of port 32 and 34.

Typically, process fluid, such as a heated liquid, gas, steam, and the like (or cooling fluid) flows through tubes 10 disposed in the interior of housing 4 between end caps 6 and 8, while cooling fluid (or process fluid) flows through the interior of heat exchanger 2, in contact with the exterior of tubes 10, between ports 32 and 34. Because of the construction of housing 4, process fluid and cooling fluid do not come into contact with each other as they pass through heat exchanger 2.

Because of the lengths of tubes 10, it is impractical to perform physical inspection of or otherwise work on said tubes. Moreover, because of the high pressures typically involved it is necessary to identify in advance of a failure whether a tube 10 is exhibiting a symptom indicative of an impending failure. To this end, it is well known in the art to perform non-destructive testing of such tubes via eddy current probes. Eddy current probes and the use thereof for detecting and pinpointing flaws in tubing, such as tubes 10, is well known in the art and will not be described further herein for the purpose of simplicity. Hereinafter, the present invention will be described in connection with the use of an eddy current probe for performing eddy current inspection of one or more tubes 10 in communication with one or more holes 18 in tubesheet 12 or 14. However, this is not to be construed as limiting the invention since it is envisioned that the present invention can also be utilized in connection with, without limitation, a tool which inserts a plug into the end of a tube 10, a tool for cleaning the interior of a tube 10, a tool for adding a sleeve to a tube 10, a tool for repairing (e.g., welding) a tube 10, a tool for inspecting a tube 10, a tool for sleeving a tube, a tool for stabilizing a tube, and/or any other tool that can work on a tube 10. Herein, "work" or "working" on a tube 10 means any act or action that can be performed on a tube 10 including, without limitation, inspection, testing, plugging, cleaning, sleeving, repairing, stabilizing, and the like.

The present invention will now be described with reference to FIGS. 2 and 3 and with continuing reference to FIGS. 1A-1C.

In certain applications, it is not only desirable but necessary to perform robotic eddy current inspection of the tubes 10 of the internal assembly A of heat exchanger 2, for example, where the fluid passing through tubes 10 is radioactive, such as the water used to cool nuclear reactors. In an example of a system and method for eddy current testing of tubes 10 of heat exchanger 2, a robot 36 is mounted to or positioned in operative relation to tubesheet 12 (or tubesheet 14). For the purpose of this example, it will be assumed that robot 36 is mounted to tubesheet 12. However, this is not to be construed as limiting the invention since it is envisioned that robot 36 can also or alternatively be mounted to tubesheet 14.

In an example, robot 36 is a multi-axis robot having two or more axes of motion. In the illustrated example, robot 36 has axes of rotation 38 and 40 and a motor driven base unit 42 which is rotatable about axis 38, as shown by arcuate arrow 45. Robot 36 can be position in operable relation to tubesheet 12 in any suitable and/or desirable manner. In an example, base unit 42 is coupled to tubesheet 12 via a base plate 44 and suitable hangers or fasteners. The manner in which robot is positioned on or in operable relation to tube 12 is not to be construed as limiting the invention.

Figure 2:
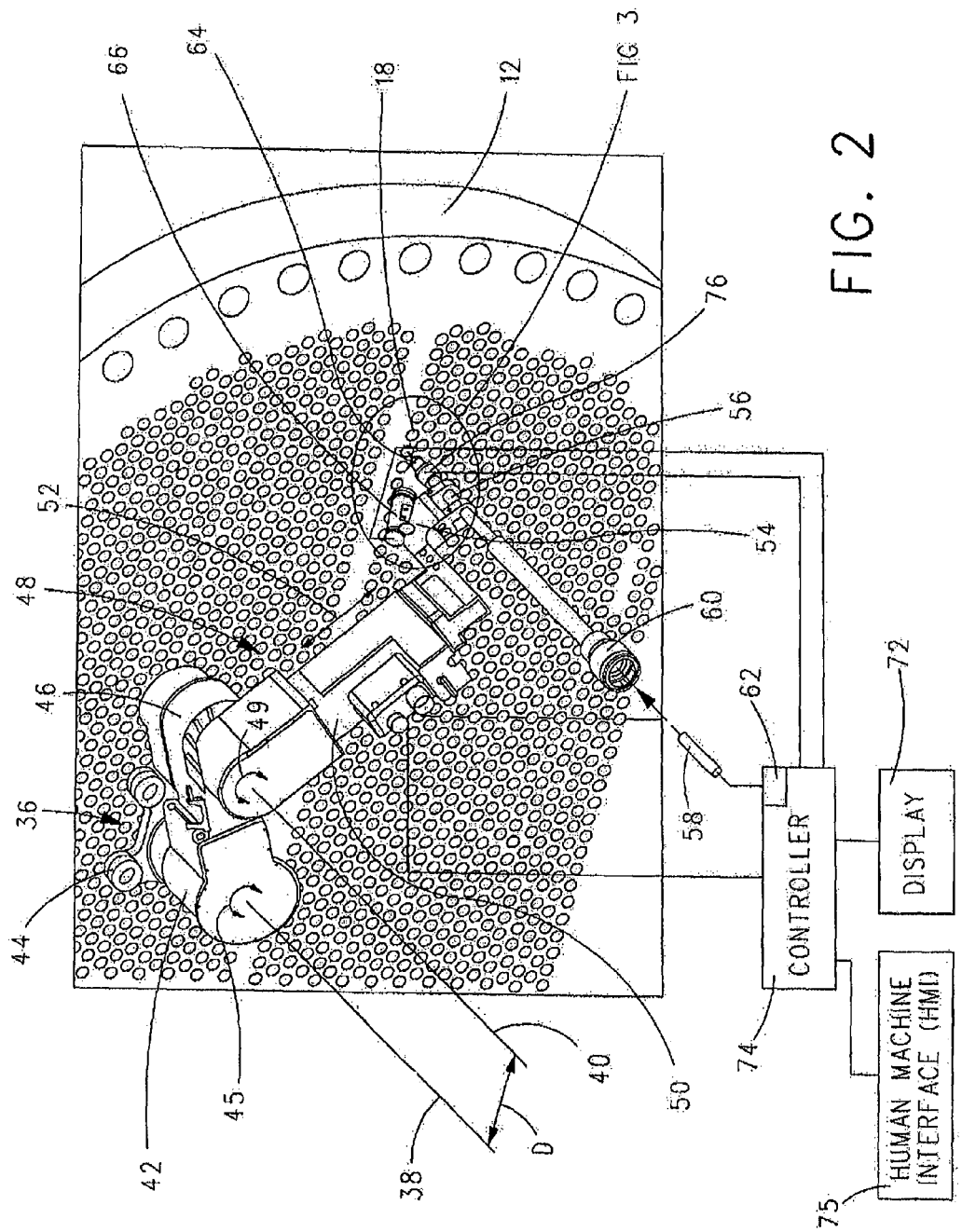
FIG. 2 is a perspective view of a robotic system for working one or more tubes of the internal assembly of FIGS. 1B-1C coupled to the tubesheet of FIGS. 1B-1C, wherein each tube is in fluid communication with one of the holes of the tubesheet.
Figure 3:
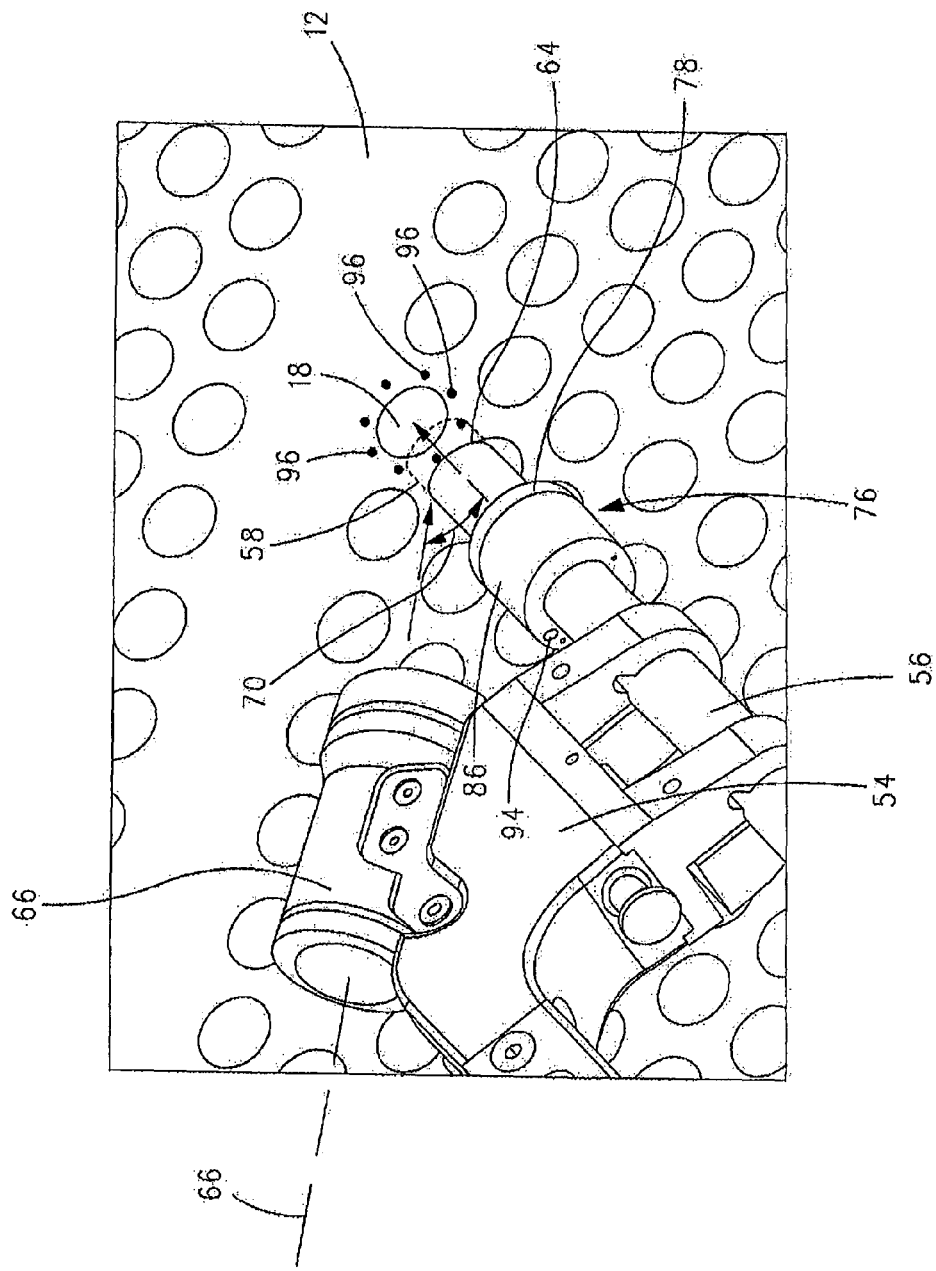
FIG. 3 is an enlarged view of the circled portion of FIG. 2.

The example robot 36 shown in FIG. 2 also includes a motorized intermediate drive unit 46 that can rotate an arm 48 of robot 36 about axis 40, as shown by arcuate arrow 49.

As shown in FIG. 2, axis 40 is separated from axis 38 by a distance D whereupon intermediate drive unit 46 can be rotated by base drive unit 42 about axis 38 while, simultaneously or separately, intermediate drive unit 46 can rotate arm 48 about axis 40. Finally, arm 48 can include a linear drive 50 that facilitates the movement of arm 48 linearly toward and away from intermediate drive unit 46 in the directions shown by arrow 52. By way of robot 36, eddy current probe testing of one or many tubes 10 via tubesheet 12 (or tubesheet 14) can be accomplished in the manner described herein.

An end-effector 54 is coupled to the end of arm 48 opposite intermediate drive unit 46. A guide-tube 56 is supported by robot 36 and, more specifically, by end-effector 54. Guide-tube 56 is hollow and is configured to receive an eddy current probe 58 therein. In use, eddy current probe 58 is introduced into end 60 of guide-tube 56 and is advanced through the lumen of guide-tube 56 by a motorized drive 62 until eddy current probe 58 exits end 64 of guide-tube 56 for entry into a tube 10 in alignment with the hole 18 that is aligned with guide-tube 56 and eddy current probe 58. In one example, the axes of eddy current probe 58, guide-tube 56, hole 18, and tube 10 in communication with hole 18 are coaxial, or substantially coaxial (subject to minor variances in the tolerances thereof). However, this is not to be construed as limiting the invention.

To facilitate the alignment of guide-tube 56 and hole 18 in a way that enables eddy current probe 58 to be inserted into the tube 10 in fluid communication with hole 18, a camera 66 is coupled to robot 36, e.g., to end-effector 54. Camera 66 is aimed at end 64 of guide-tube 56. Because of the arrangement of eddy current probe 58, guide-tube 56, hole 18, and the tube 10 in communication with hole 18, the viewing axis 68 of camera 66 is offset at an angle 70 from the axis of guide-tube 56. Because of angle 70, an image acquired by camera 66 and displayed on a display 72 suffers from a condition known as parallax, namely, the apparent displacement of an observed object due to the change in position of the observer, in this case, camera 66.

Because of this parallax, an image acquired by a controller 74 and either used thereby and/or displayed on display 72 for observation by a human operator cannot be accurately relied upon for ensuring that the guide-tube 56 is aligned with hole 18 and the tube 10 in fluid communication with hole 18. In this regard, a human machine interface (HMI) 75 can be provided and coupled to controller 74 whereupon a user viewing an image acquired by camera 66 and displayed on display 72 can utilize HMI 75 to control robot 36 to move guide-tube 56 into alignment with hole 18 in a manner known in the art. Also or alternatively, controller 74 can be programmed to automatically align guide-tube 76 with hole 18. Also or alternatively, it is envisioned that some combination of the programming of controller 74 and a user via display 72 and HMI 75 can be utilized to automatically and manually position guide-tube 56 in alignment with hole 18. For example, it is envisioned that controller 74 operating under the control of a control program can cause robot 36 to move guide-tube 76 into coarse or rough alignment with one of the holes 18 of tubesheet 12. Thereafter, via display 72 and HMI 75, an operator can refine the alignment of guide-tube in alignment with the hole 18, i.e., perform fine alignment of guide-tube 56 into alignment with hole 18 of tubesheet 12.

To facilitate the accurate automated, manual, or combination of automated and manual alignment of eddy current probe 58 and guide-tube 56 to one or more holes 18 of tubesheet 12, a laser collar 76 or other comparable light source can be disposed on end-effector 54 and, more particularly, guide-tube 56, desirably adjacent end 64 of guide-tube 56.

Figure 4:
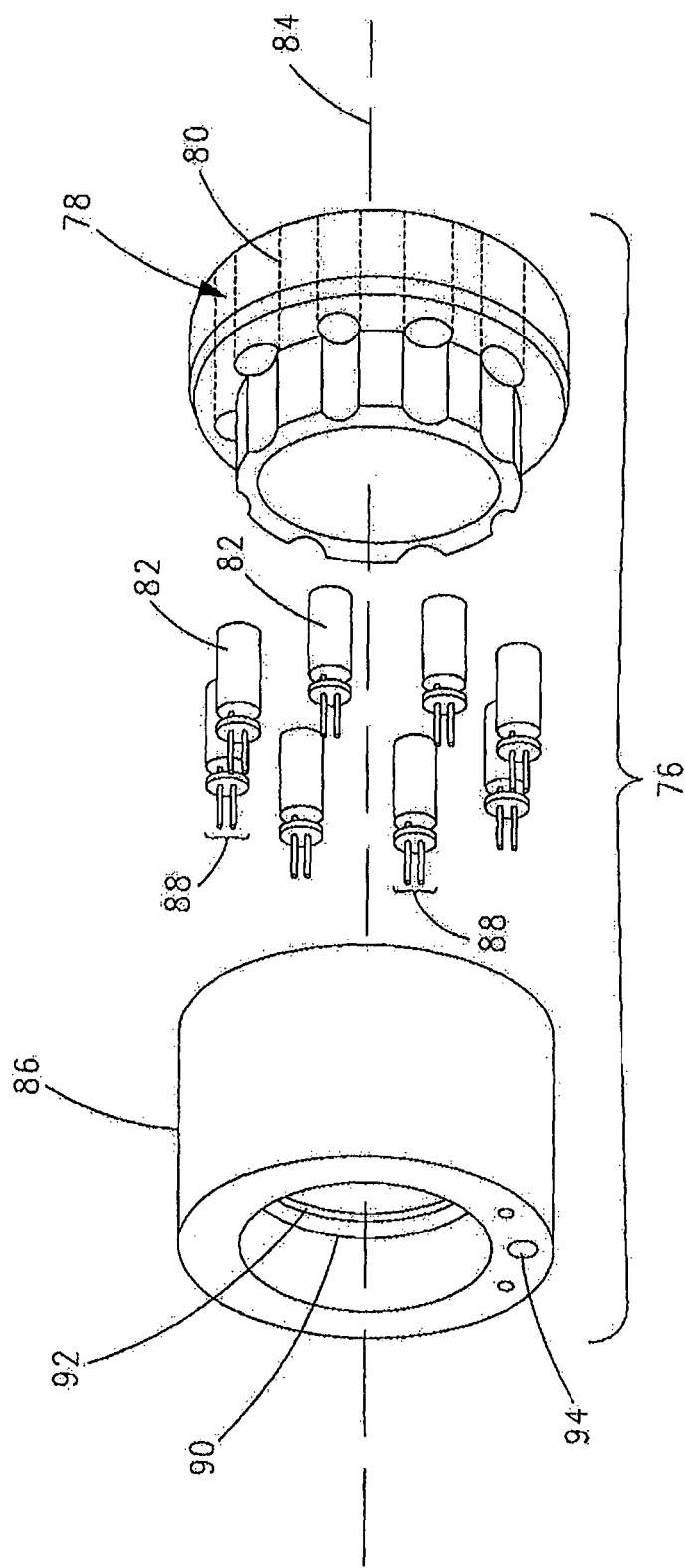
FIG. 4 is an exploded perspective view of the laser collar shown in FIGS. 2 and 3.

With reference to FIG. 4 and with continuing reference to all previous figures, laser collar 76 includes a collar element 78 that includes a plurality of holes 80 around the outer circumference of collar 76, with each hole 80 adapted to receive and support a laser diode 82 in a manner such that, when laser collar 76 is mounted on guide tube 56, a laser beam output by each laser diode 82 is projected toward tubesheet 12. In an example, when laser collar 76 is disposed on guide-tube 56 the laser beam output by each laser diode 82 is parallel or substantially parallel to a central axis 84 of laser collar 76. Laser collar also includes a sleeve 86 configured to mate with collar 78 thereby covering the electrical connection ends 88 of laser diodes 82.

In an example, sleeve 86 can include an O-ring groove 90 for receiving an O ring 92 that facilitates frictionally holding laser collar 76 to guide-tube 56. Sleeve 86 can further include a cable hole 94 for connecting the electrical connection ends 88 of laser diodes 82 to controller 74 which can control the supplying or withholding of electrical power to or from laser diodes 82.

In an example, laser collar 76 includes eight laser diodes which, when energized by electrical power provided by controller 74, project eight laser beams toward the surface of tubesheet 12 where said laser beams interact with said surface forming light or laser spots 96 on said surface.

In an example, laser collar 76 supports laser diodes 82 in a manner such that when energized by electrical power from controller 74, laser diodes 82 form a ring of laser spots 96. Also or alternatively, in another example laser diodes 82 can be configured to form an arc of laser spots 96. In an example, the symmetry of the ring or arc of laser spots 96 about a hole 18 can be utilized to fine position the axis of guide-tube 56 with the axis of hole 18 and, hence, the tube 10 in communication with hole 18. In this regard, if the ring or arc of laser spots 96 (an arc of laser spots 96 being a subset of a ring of laser spots 96) are not symmetrical about hole 18, the position of guide-tube 56 can be moved by robot 36 automatically under the control of controller 74 and/or via an operator observing an image acquired by camera 66 and displayed on display 72 and HMI 75. The process of fine positioning guide-tube 56 can continue until it is determined via an image acquired by camera 66 that the arc or ring of laser spots 96 is positioned symmetrically about hole 18.

A method of working, e.g., without limitation, eddy current inspecting, tubes 10 coupled to tubesheet 12 having a plurality of holes 18, with each hole 18 in fluid communication with one of the tubes 10 will now be described.

Initially, robot 36 is positioned in operable relation to tubesheet 12 with end-effector 54 and guide-tube 56 supported by robot 36. Eddy current probe 58 is supported by and, more particularly, by guide-tube 56 and is movable relative to end-effector 54 and, more particularly, to guide-tube 56, e.g., slidable in the interior of guide-tube 56. Camera 66 is coupled to robot 36 and, more particularly, to end-effector 54, and a plurality of lasers 82 (in an example, supported by laser collar 76) is positioned on end-effector 54 and, more particularly, around an exterior of guide-tube 56. The lasers are operable to output a plurality of laser beams toward tubesheet 12.

Via robot 36, end-effector 54 and guide-tube 56 are positioned in coarse alignment with a first hole 18 in tubesheet 12. Thereafter, via camera 66, a pattern of laser spots 96 formed by the projection of the laser beams on the surface of tubesheet 12 adjacent the first hole 18 in tubesheet 12 is detected. Next, via robot 36, the alignment of end-effector 54 and, more particularly, guide-tube 56 in alignment with the first hole 18 in tubesheet 12 is refined based on the detected pattern of laser spots 96 formed on the surface of tubesheet 12. More particularly, the alignment of the guide-tube 56 with the first hole 18 in tubesheet 12 is refined based upon the symmetry of the detected pattern of laser spots 96 formed on the surface of the tubesheet 12. Thereafter, via motorized drive 62, under the automatic or manual (via HMI 75) control of controller 74, eddy current probe 58 (shown in phantom in FIG. 3) is moved from the interior of guide-tube 56 into the tube 10 that is fluid communication with the first hole 18 in the tubesheet.

During working or eddy current testing of the tube 10, motorized drive 62 is controlled to move eddy current probe 58 along the length of tube 10 during the acquisition of eddy current data by controller 74. Upon completion of eddy current testing of tube 10, eddy current probe 58 is withdrawn into guide-tube 56 from the tube 10 that is in fluid communication with the first hole 18 in tubesheet 12.

Thereafter, as desired, the foregoing steps can be repeated for one or more other holes 18 of tubesheet 12 by way of robot 36 moving end-effector 54 and, more particularly, guide-tube 56 into alignment with said one or more other holes 18 of tubesheet 12 (or tubesheet 14).

In an example, the step of positioning end-effector 54 and, more particularly, guide-tube 56 in coarse alignment with the each hole 18 can be based upon X, Y coordinates of said hole 18 programmed into controller 74 which automatically controls robot 36 to move end-effector 54 and, more particularly, guide-tube 58 into coarse alignment with said hole 18. Thereafter, the fine alignment of end-effector 54 and, more particularly, guide-tube 56 in alignment with each hole in tubesheet 12 can be refined automatically by controller 74 using standard computer vision techniques based on an image acquired by camera 66 or by a human operator via HMI 75 and an image acquired by camera 66 and displayed on display 72.

In a non-limiting example, prior to moving eddy current probe 58 into a tube 10 in fluid communication with a hole 18 in tubesheet 12, the eddy current probe 58, the guide-tube 56, the hole 18, and the tube 10 in fluid communication with the hole 18 are aligned, e.g., without limitation, coaxially or substantially coaxially, whereupon minor variances in the alignment of eddy current probe 58, guide-tube 56, hole 18, and tube 10 in fluid communication with hole 18 do not affect the movement of eddy current probe 58 into the tube 10 that is in fluid communication with the hole 18 in tubesheet 12.

In the illustrated embodiment, robot 36 has two axes of rotation and one axis of linear motion. However, this is not to be construed as limiting the invention since it is envisioned that a robot having any suitable and/or desirable number of axis or axes of rotation or axis or axes of linear motion that is capable of moving guide-tube 56 into alignment with any number of holes 18 of tubesheet 12 can be utilized.

In an embodiment, the pattern of laser spots 96 formed on the surface of tubesheet 12 can be an arc or a ring of laser spots about, around, or adjacent a hole 18. The refining of the alignment of guide-tube 56 in alignment with the hole 18 in tubesheet 12 can be based upon the symmetry of the arc or ring of laser spots about, around, or adjacent the hole 18. In another, more general example of eddy current inspection of tubes 10 coupled to tubesheet 12 having a plurality of holes 18, with each hole 18 in fluid communication one of the tubes 10, eddy current probe 58 is positioned in alignment with a hole 18 in tubesheet 12. A plurality of spots of light 96 is projected onto a surface of tubesheet adjacent the hole 18. Eddy current probe 58 is then moved into the tube 10 that is in fluid communication with the hole 18 in tubesheet 12.

The alignment of eddy current probe 58 in alignment with the hole 18 in tubesheet 12 can be refined based on a symmetry of the spots of light 96 projected onto the surface of the tubesheet 12 about the hole 18.

Upon completion of eddy current testing of the tube 10, eddy current probe 58 can be withdrawn from the tube 10 that is in fluid communication with the hole 18 in the tubesheet 12.

Any one or combination of the steps of positioning the eddy current probe, projecting the plurality of light spots, refining the alignment of the eddy current probe, moving the eddy current probe into the tube, and/or withdrawing the eddy current probe from the tube can be repeated for one or more other holes 18 of tubesheet 12.

In an example, the spots of lights can define an arc or ring of light spots. The refining of the alignment of the eddy current probe in alignment with a hole 18 in tubesheet 12 can include refining the symmetry of the arc or ring of light spots about the hole 18.

As can be seen, guide-tube 56 must be positioned sufficiently in alignment with the tube 10 to be inspected and the hole 18 in the tubesheet in alignment with the tube 10 to be inspected in order for eddy current probe 58 to run smoothly out of guide-tube 56 and into the hole 18 in the tubesheet in alignment with the tube 10 to be inspected. The position of the end 64 of guide-tube 56 is remotely monitored using camera 66. The parallax of the camera view makes it difficult to determine when guide-tube 56 is positioned in alignment with the hole of tubesheet 12 and the tube 10 in alignment therewith.

To overcome this, laser diodes 82 mounted on end-effector 54 and, more particularly, guide-tube 56 are aimed at tubesheet 12. When the hole 18 of tubesheet 12 is positioned relative to the laser spots 96 formed on the surface of tube 12, end-effector 54 and, more particularly, guide-tube 56 is in operative position with the hole 18 and the tube 10 in alignment with hole 18.

In addition to a discrete number of laser diodes 82, other configurations of laser collar 76 can include line lasers to create a crosshair and/or a complete circle. Laser collar 76 can be used for automated or manual centering. The position of the laser spots 96 on the camera view of tubesheet 12 can be determined by blinking laser diodes 82 on and off and comparing two images, one with the lasers on and one with the lasers off. The parts of these two images that are different are the laser spots 96. Another possibility is to use a filter to find the unique color of the reflected laser spots 96. Each hole 18 in tubesheet 12 can be recognized using standard computer vision techniques. By scanning the image in the vicinity of the laser spots 96 it can be determined if the laser spots 96 are symmetric about the hole 18, and thus when guide-tube 56 is aligned with a hole 18 in tubesheet 12.

In an example, laser collar 76 can also be used to determine if eddy current probe 58 is in or out of a tube 10. This is important since robot 36 must not be moved while eddy current probe 58 is in a tube 10 as this would destroy the eddy current probe 58. This can be done by automatically or manually counting the laser spots 96 on the surface of tubesheet 12. If the eddy current probe 58 is in a tube 10, at least one of the laser spots 96 will be blocked by the eddy current probe 58 or the cable coupled thereto.

The present invention has been described with reference to exemplary non-limiting embodiments. Obvious modifications and alterations will occur to others upon reading and understanding the preceding detailed description. For example, eddy current probe 58 is but one example of a tool that can be used for working tubes 10 coupled to a tubesheet. In this regard, other tools that can be utilized with or in a replacement of eddy current probe 58 include, without limitation, tools for plugging, cleaning, sleeving, repairing, inspection and/or stabilizing of tubes 10 coupled to tubesheet 12. Accordingly, the present invention is not to be construed as limited to the tool described in the above example, namely, an eddy current probe 58. Finally, some tools may not require the use of guide tube 56 or the use of a guide tube 56 is optional to work a tube 10. Accordingly, with such tools, a guide tube 56 is either not used or the use of a guide tube 56 is optional. It is envisioned that the invention be construed as including all such modifications and alterations insofar as they come within the scope of the appended claims or the equivalents thereof.

The invention claimed is:

1. A method of working tubes coupled to a tubesheet having a plurality of holes, each hole in fluid communication with one of the tubes, the method comprising:
   (a) providing a robot positioned in operable relation to the tubesheet, a guide-tube supported by the robot, a tool supported by the guide-tube and movable relative to the guide-tube, a camera coupled to the robot, and a plurality of lasers positioned around an exterior of the guide-tube and operable to output a plurality of laser beams toward the tubesheet;
   (b) the robot positioning the guide-tube in coarse alignment with a first hole in the tubesheet;
   (c) the camera detecting a pattern of laser spots formed by the laser beams on a surface of the tubesheet adjacent the first hole in the tubesheet;
   (d) the robot refining the alignment of the guide-tube in alignment with the first hole in the tubesheet based on the detected pattern of laser spots formed on the surface of the tubesheet; and
   (e) moving the tool into the tube that is in fluid communication with the first hole in the tubesheet.

2. The method of claim 1, further including:
   (f) withdrawing the tool from the tube that is in fluid communication with the first hole in the tubesheet.

3. The method of claim 2, further including repeating steps (b)-(f) for at least one other hole of the tubesheet.

4. The method of claim 1, wherein, the positioning in step (b) is with or without reference to the laser spots formed by the laser beams on the surface of the tubesheet.

5. The method of claim 1, wherein, following step (d), the guide-tube, the tool, the first hole, and the tube that is in fluid communication with the first hole are positioned coaxially.

6. The method of claim 1, wherein the robot has two axes of motion.

7. The method of claim 1, wherein the camera has a viewing axis that is non-parallel with an axis of the first hole.

8. The method of claim 1, wherein:
   the pattern of laser spots is an arc or a ring of laser spots adjacent the first hole; and
   step (d) includes refining the alignment of the guide-tube in alignment with the first hole in the tubesheet based on a symmetry of the arc or a ring of laser spots around the first hole.

9. The method of claim 1, further including, following step (e), determining one of the following:
   that the tool is out of the tube based on being able to observe the entire light pattern; and
   that the tool is in the tube based on not being able to observe the entire light pattern.

10. A method of working tubes coupled to a tubesheet having a plurality of holes, each hole in fluid communication with one of the tubes, the method comprising:
    (a) positioning a tool in alignment with a first hole in the tubesheet;
    (b) projecting a light pattern onto a surface of the tubesheet adjacent an outer boundary of the first hole;
    (c) refining the alignment of the tool in alignment with the first hole in the tubesheet based on a symmetry of the light pattern projected onto the surface of the tubesheet about the first hole; and
    (d) moving the tool into the tube that is in fluid communication with the first hole in the tubesheet based on the projected light path, wherein
    the light pattern defines an arc or a ring of light; and
    step (c) includes refining the symmetry of the arc or ring of light about the first hole.

11. The method of claim 10, further including:
    (e) withdrawing the tool from the tube that is in fluid communication with the first hole in the tubesheet based on the projected light pattern.

12. The method of claim 11, further including repeating steps (a)-(e) for a plurality of other holes of the tubesheet.

13. The method of claim 10, wherein the light pattern is one of the following: a plurality of spots of light, a cross hair, or a circle.

14. The method of claim 13, wherein the plurality of spots of light includes light spots of different colors.

15. The method of claim 10, wherein refining the alignment of the tool with the first hole in the tubesheet further includes turning the light pattern on and off.

16. The method of claim 10, further including, following step (d), determining one of the following:
    that the tool is out of the tube based on being able to observe the entire light pattern; and
    that the tool is in the tube based on not being able to observe the entire light pattern.

* * * * *